United States Patent
Kuo et al.

(10) Patent No.: US 8,244,390 B2
(45) Date of Patent: Aug. 14, 2012

(54) SYSTEM AND METHOD FOR IMPROVED DENTAL GEOMETRY REPRESENTATION

(75) Inventors: Eric Kuo, Foster City, CA (US); Vadim Matov, San Jose, CA (US); Jihua Cheng, Cupertino, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 12/961,818

(22) Filed: Dec. 7, 2010

(65) Prior Publication Data

US 2011/0077913 A1 Mar. 31, 2011

Related U.S. Application Data

(62) Division of application No. 11/951,812, filed on Dec. 6, 2007, now Pat. No. 7,865,259.

(51) Int. Cl.
*G06F 19/00* (2011.01)

(52) U.S. Cl. .............................. 700/98; 433/24; 433/213

(58) Field of Classification Search .................... 433/23, 433/213, 215; 700/98; 382/154; 356/601
See application file for complete search history.

(56) References Cited

U.S. PATENT DOCUMENTS

| | | | |
|---|---|---|---|
| 5,121,333 A * | 6/1992 | Riley et al. ..................... 700/163 |
| 7,068,825 B2 * | 6/2006 | Rubbert et al. ................ 382/128 |
| 2001/0002310 A1 * | 5/2001 | Chishti et al. .................... 433/24 |
| 2004/0220691 A1 * | 11/2004 | Hofmeister et al. ............. 700/98 |

* cited by examiner

*Primary Examiner* — Chris L Rodriguez
*Assistant Examiner* — Eric Rosen
(74) *Attorney, Agent, or Firm* — Klein, O'Neill & Singh, LLP

(57) ABSTRACT

A digital data set representing a pre-scanned tooth geometry, including digital data representing a digitally-mirrored contralateral digital tooth model including a crown component, is merged with data representing a scanned patient tooth crown image which lacks sufficient data to completely represent a complete tooth crown to create a complete digital tooth crown model.

9 Claims, 9 Drawing Sheets

CONTOUR A
MODELING

CONTOUR B
X-RAY

CONTOUR A
WITH LANDMARKS

CONTOUR B
AFTER SCRUBBING
WITH LANDMARKS

CONTOUR B
AFTER MORPHING

SYSTEM AND METHOD FOR IMPROVED DENTAL GEOMETRY REPRESENTATION

CROSS REFERENCE TO RELATED APPLICATIONS

This application is a divisional application of application Ser. No. 11/951,812, filed Dec, 6, 2007, now U.S. Pat. No. 7,865,259, the disclosure of which is incorporated herein in its entirety.

BACKGROUND

1. Field of the Invention

The present invention relates, generally, to dental and/or orthodontic treatment, and in particular to a system and method for modeling a complete tooth of a patient to facilitate dental and/or orthodontic treatment.

2. Related Art

Current techniques for impression-based computational orthodontics are based on impressions, three dimensional (3-D) radiographic scans or 3-D x-rays of teeth, which capture the surface of the teeth. Unfortunately, when two or more teeth are in close proximity, the digital data representing surfaces of the individual teeth are difficult to separate when using these techniques. The same problem exists for "unerupted" teeth, where the initial scan may capture only exposed portions of the teeth.

The inability to account accurately for the interproximal and unerupted surfaces of the teeth means that aligners created based on the incomplete data may not properly fit in the areas that are later exposed either through eruption from the gingiva, uncrowding, or improved hygiene, which may firm up the gingival tissue and expose more tooth structure. An aligner that does not fit well becomes less effective in later stages of the orthodontic treatment. A poorly fitting aligner may also compromise the esthetics of the appliance, which in turn, may lead to suboptimal patient compliance in wearing the aligners.

SUMMARY

In accordance with various aspects of the present invention, a system and method are provided to account for the interproximal and unerupted surfaces of teeth that are partially blocked or unexposed in impressions, 3-D radiographic scans or 3-D X-rays to facilitate dental and/or orthodontic treatment.

In one aspect, a digital data set representing a pre-scanned tooth geometry, including generic crown data, is merged with data representing a scanned patient tooth crown image, which lacks sufficient data to completely represent a complete tooth crown.

This brief summary has been provided so that the nature of the invention may be understood quickly. A more complete understanding of the invention may be obtained by reference to the following detailed description in connection with the attached drawings.

BRIEF DESCRIPTION OF THE DRAWINGS

The foregoing features and other features of the present invention will now be described with reference to the drawings. In the drawings, the same components have the same reference numerals. The illustrated embodiment is intended to illustrate, but not to limit the invention. The drawings include the following Figures.

DETAILED DESCRIPTION

Figure 1A:
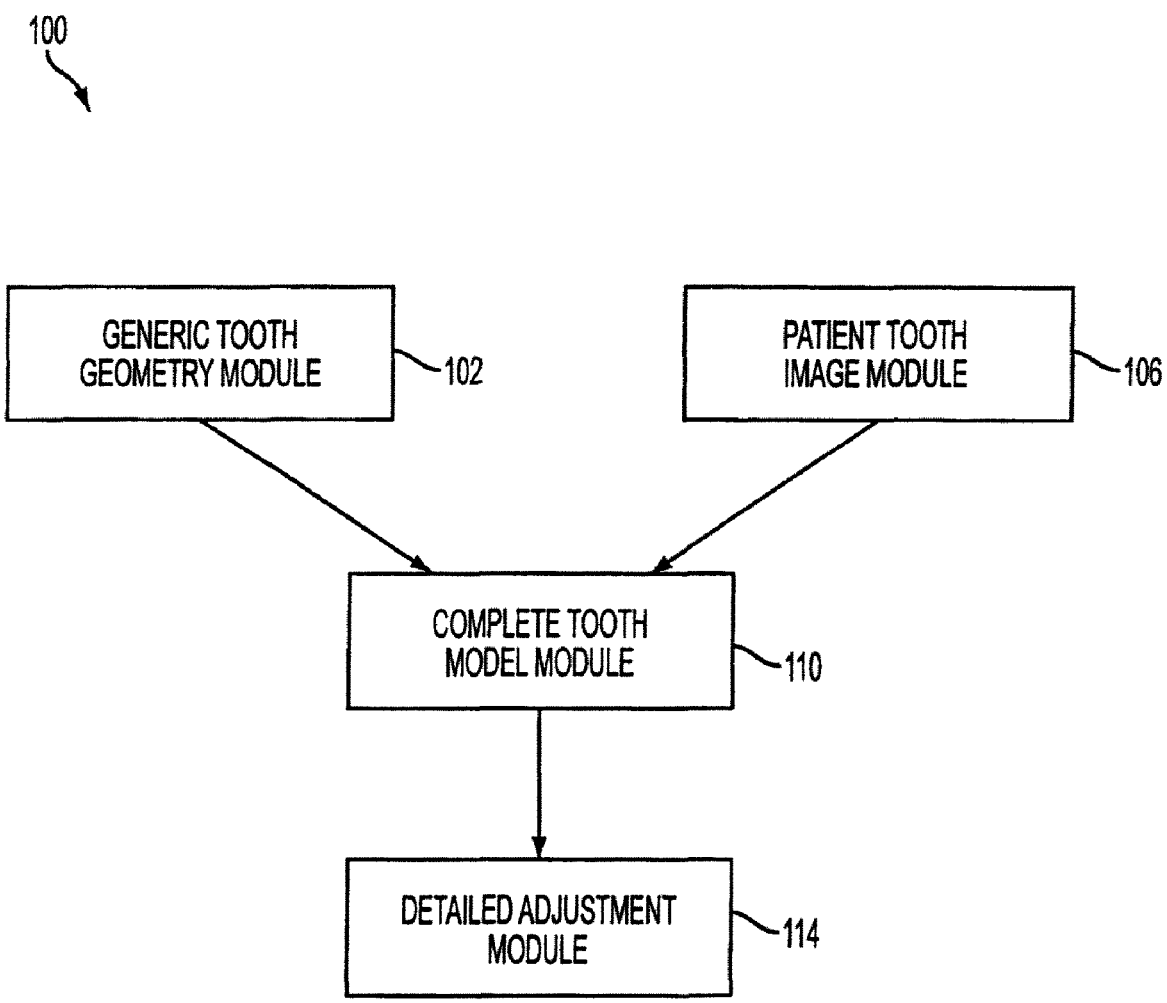
FIG. 1A is a flow diagram of a process for creating a complete tooth model from tooth images of teeth having partially blocked or unexposed surfaces in accordance with an embodiment of the present invention.

The present invention may be described herein in terms of various components and processing steps. It should be appreciated that such components and steps may be realized by any number of hardware and software components configured to perform the specified functions. For example, the present invention may employ various electronic control devices, visual display devices, input terminals and the like, which may carry out a variety of functions under the control of one or more control systems, microprocessors or other control devices.

In addition, the present invention may be practiced in any number of orthodontic or dental contexts and the exemplary embodiments relating to a system and method for modeling of complete tooth of a patient as described herein are merely a few of the exemplary applications for the invention. For example, the principles, features and methods discussed may be applied to any orthodontic or dental treatment application or process.

For illustrative purposes, the various exemplary methods and systems may be described in connection with a single tooth of a patient; however, such exemplary methods and systems may be implemented on more than one tooth and/or all teeth within a patient, such as molars, bicuspids, canines, incisors or any other teeth. For example, the exemplary methods and systems may be implemented by performing a particular process, operation or step on one or more teeth before proceeding to a subsequent process, operation or step, or by performing all or essentially all processes, operations or steps on a particular tooth before proceeding to another tooth, or any combination thereof.

In one embodiment, the present invention includes taking a digital data set representing a scanned typodont tooth geometry and using the data by combining or merging the data with digital data representing a partially erupted or partially blocked tooth crown. By using the two sets of data by, for example, digitally combining or merging the digital typodont tooth model to the digital scanned tooth crown model, the blocked or unexposed surfaces of the patient crown may be completed using the typodont tooth geometry to "fill-in" the missing tooth crown surface. Such a process may be applied for any and all of the various teeth within a patient, such as molars, bicuspids, canines, incisors or any other teeth.

In another embodiment of the invention, a digital data set representing a scanned tooth of the patient from the contralateral side is digitally mirrored and combined or merged with data representing a scanned tooth crown image which lacks sufficient data to completely represent a complete tooth crown.

In another embodiment of the invention, a digital data set representing a scanned tooth of a patient having similar dentition is combined with data representing a scanned tooth crown image which lacks sufficient data to completely represent a complete tooth crown.

In another embodiment, the present invention includes taking the digital data set representing a similar tooth but from a different patient and combining or merging the data with data representing a scanned tooth crown image which lacks sufficient data to completely represent a complete tooth crown.

Such modeling techniques may be conducted with one or more computer-based systems, such as systems configured for storing actual patient data and generic tooth data, morphing generic tooth data to such patient's data and/or facilitating additional orthodontic treatment applications, through the use of one or more algorithms.

Figure 1B:
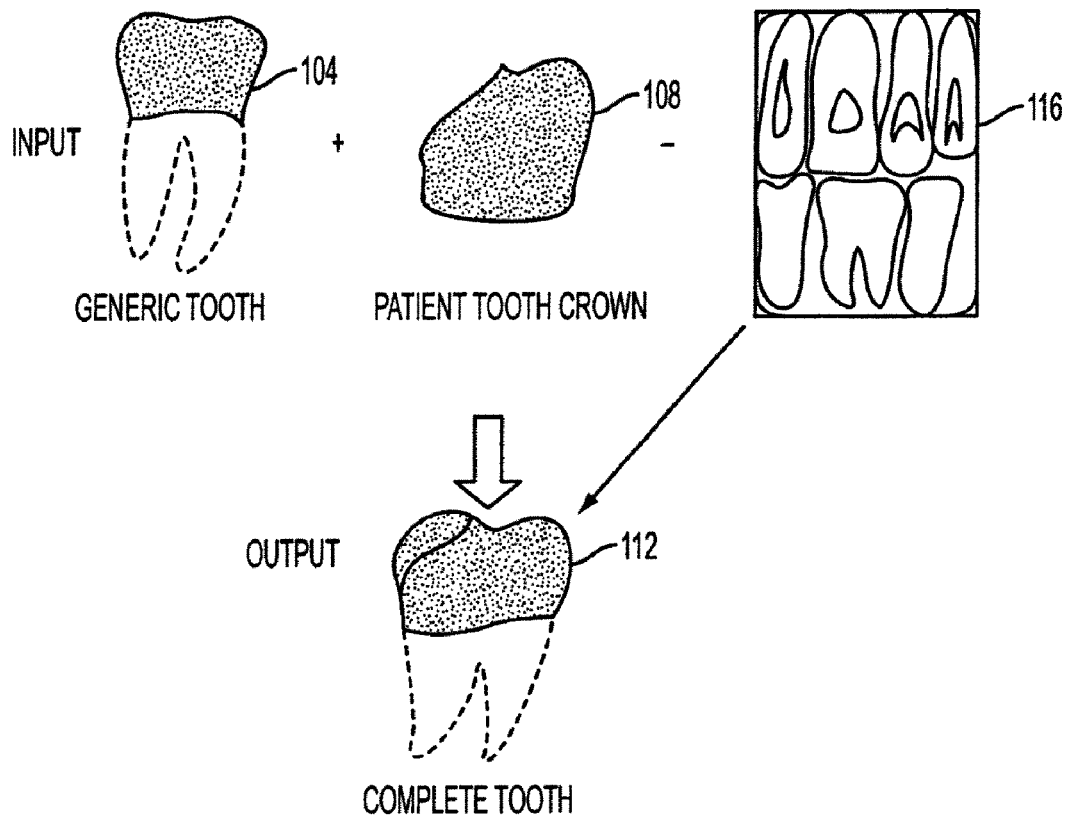
FIG. 1B is composed of images illustrating the process of FIG. 1A for creating a complete tooth model from tooth images of teeth having partially blocked or unexposed surfaces in accordance with an embodiment of the present invention.

FIGS. 1A and 1B illustrate a process 100 for creating a complete tooth model in a digital format from tooth images that are created from teeth having partially blocked or unexposed surfaces in accordance with the present invention. In one embodiment, process 100 includes a typodont tooth geometry module 102 for creating a digital data set representing a generic typodont, including crown geometry and, optionally root geometry, such as generic tooth model 104 (FIG. 1B). Process 100 also includes patient tooth image module 106 for creating a digital data set representing a surface image of a crown of a patient with an incomplete surface portion, such as patient tooth crown 108. In complete tooth model module 110 the typodont tooth surface geometry data set generated in module 102 is "combined" or "merged," (also "morphed" or "stitched") to the patient's incomplete surface image data set generated in module 106 to yield a complete tooth image data set, such as 3-D complete tooth model 112.

In one embodiment, further adjustment of the complete tooth model 112 may be provided through detailed adjustment module 114. For example, additional patient information regarding the actual crown of a patient may be obtained, such as from 3-D radiographic images 116 and the like. The scanned images may be used as the basis for morphing geometries to the scanned images to address variations in tooth shape between the generic tooth 104 and the partially represented actual tooth shape 108 so as to yield a tooth shape on complete tooth model 112 which more closely approximates the actual tooth.

In typodont tooth geometry module 102, a generic typodont tooth surface geometry model (which may include a generic root structure) may be scanned using well known destructive scanning techniques, to provide the digital data representing the generic typodont tooth surface geometry. Typically, the generic typodont tooth surface geometry data represents the same type of tooth (e.g. molar, canine, bicuspid, incisor and the like) as the actual tooth image it is intended to model, and may also be the same numbered tooth as the actual patient tooth, using conventional tooth numbering and identification systems.

In patient tooth image module 106, data sets representing a patient's tooth crown may be generated by various techniques for creating a tooth crown image, such as those disclosed in U.S. Pat. No. 6,685,469, assigned to Align Technology, Inc. (the "'469 patent"), herein incorporated by reference, in its entirety, for all purposes, or such modeling processes known and provided under the brands INVISALIGN® and CLINCHECK® that are available from Align Technology, Inc. of Santa Clara, Calif.

The creation of the complete tooth model 112 in complete tooth model module 110 may be realized by combining or merging the data from tooth geometry module 102 and patient tooth image module 106, such as by a computer algorithm within a tooth model system, for the creation of a complete tooth, with such processes being applied to any or all teeth within the patient.

Figure 1C:
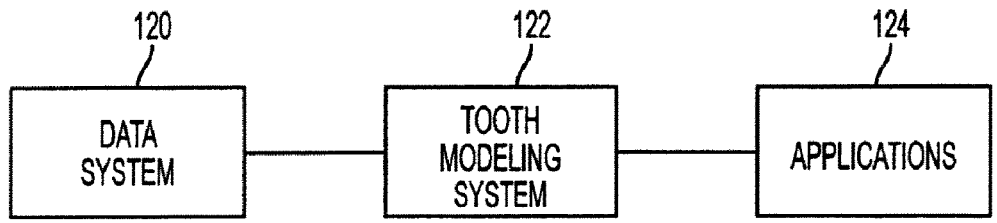
FIG. 1C illustrates a system for implementing the process of FIGS. 1A and 1B in accordance with an embodiment of the present invention.

As shown in FIG. 1C, exemplary modeling methods may be conducted with one or more computer-based systems, for example, a system 120 configured for storing patient data and generic tooth data. Also, a tooth modeling system 122 configured for executing generic tooth module 102 and patient tooth crown module 106 and for merging data and information generated from modules 102 and 106 to generate complete tooth model 112 in complete tooth model module 110. A system 124 may be configured for facilitating any other conventional orthodontic treatment applications, such as methods or processes for tracking teeth movement and position, evaluating gingival effects, or any other orthodontic treatment process from pre-treatment to final stages, or any stages in between.

Systems 120, 122 and/or 124 may include one or more microprocessors, memory systems and/or input/output devices for processing modeling data and information. To facilitate modeling of a patient crown, tooth modeling system 120 may include one or more software algorithms configured for generating complete tooth model 112 and/or performing other functions set forth herein.

Figure 2:
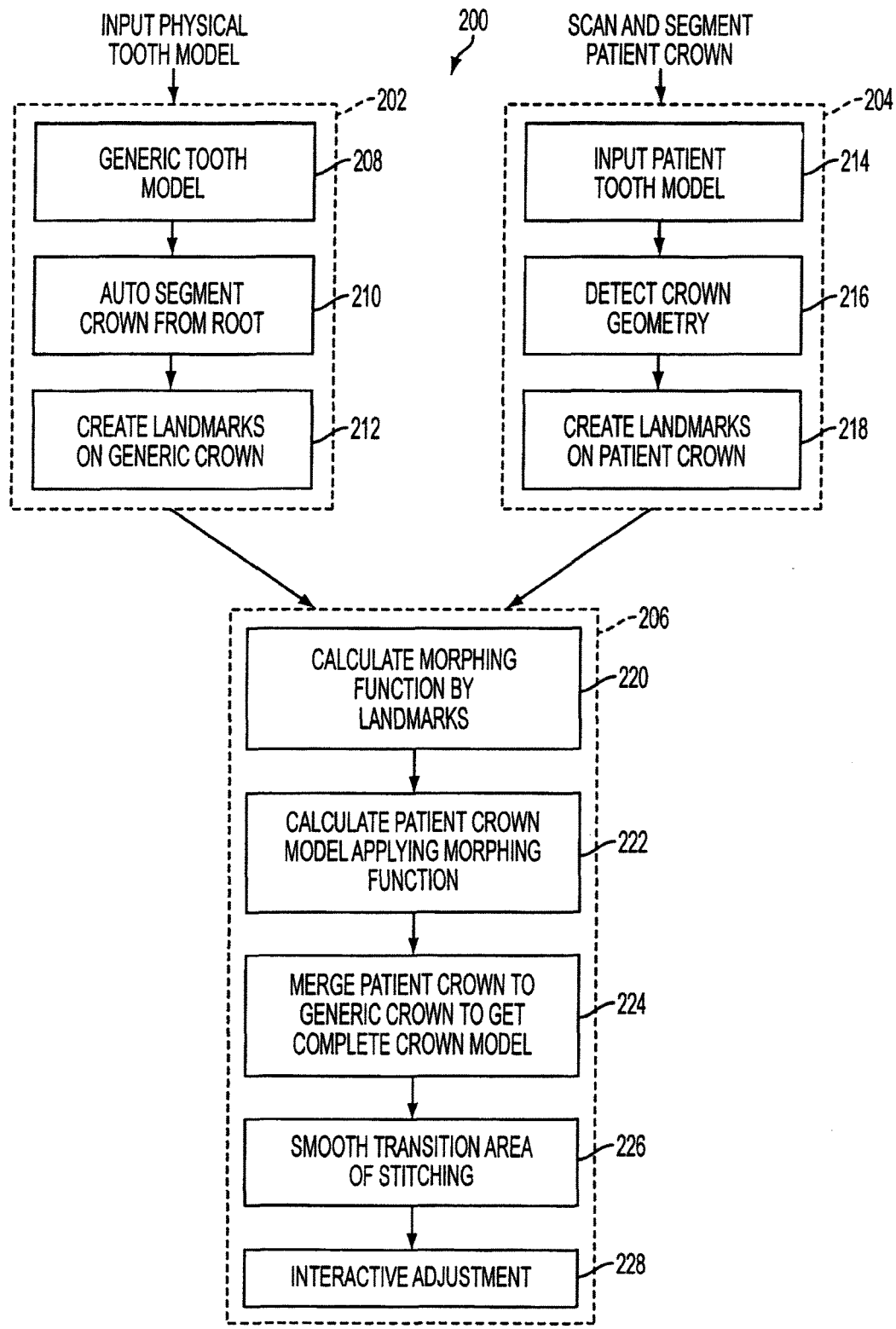
FIG. 2 is a flow diagram illustrating a computer-implemented process for modeling of a complete tooth crown model of a patient's partially blocked or unexposed crown surfaces in accordance with an embodiment of the present invention.

FIG. 2 is a flow diagram illustrating an exemplary computer-implemented process 200 for modeling of a complete tooth crown model of a patient's partially blocked or unexposed crown surfaces. Process 200 includes a method 202 for generating a generic tooth crown model, a method 204 for generating a patient tooth crown model, excluding partially blocked or unexposed crown surfaces, and a method 206 for generating a complete tooth crown model through a combination of a morphed generic tooth crown model with a corresponding patient partially complete tooth crown model.

Generic tooth modeling method 202 provides a reference for construction of generic tooth 104 (FIG. 1B), which may include both a root and a crown for a particular tooth, if desired. In one embodiment, generic tooth modeling method 202 includes the generation of a generic tooth model template 208, auto-segmenting of a generic crown from the generic root, if needed, within the generic tooth model 210, and automatic creation of landmarks on the generic crown 212.

Generation of a generic tooth model template (208) may be configured to facilitate the creation of landmarks on the generic tooth model to allow for merging with the patient tooth crown model. For example, in order to generate adequately distributed landmarks and to accurately segment the crown from the tooth, the setup of generic tooth data is provided to generate a generic tooth template as shown in FIG. 3A.

Figure 3A:
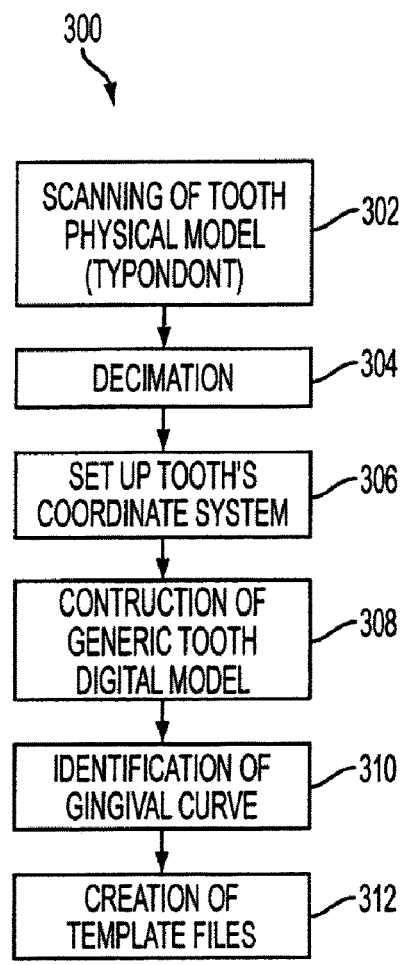
FIGS. 3A-3C illustrate a flow diagram and graphical representations of an exemplary method of modeling a generic teeth template in accordance with an exemplary embodiment of the present invention.

FIG. 3A illustrates a process 300 for generating a generic tooth model template (208) in accordance with one embodiment. Process 300 includes the acquisition of data from a physical tooth model (302), such as a typodont, the decimation of tooth model data (304), the creation of a generic tooth model coordinate system (306), the construction of a generic tooth digital model (308), the identification of gingival curves (310) and the creation of template file(s) associated with the generic tooth model (312).

The acquisition of data from a physical tooth model (302) may include the scanning of a standard typodont or any other three-dimensional models for demonstrating alignment of teeth within a patient to generate three-dimensional digital template data.

In one embodiment, a contralateral pair of a partially represented crown may be used to provide the generic tooth model. For example, as shown in FIG. 3C, tooth 314 has a contralateral pair—contralateral tooth 316—which has substantial bilateral symmetry (mirror image symmetry) to tooth 314. Thus, if a digital tooth image created from tooth 314 had a partially blocked or unexposed surface, then contralateral tooth 316 may be scanned and the digital data "mirrored" to provide a substantially symmetric tooth to tooth 314 to be used as the generic tooth model in accordance with the present invention.

In other embodiments, a scanned tooth having similar dentition or a scanned tooth having similar dentition, but from a different patient, may be used to provide the generic tooth model.

Such typodont or models that are used for scanning may include both an exemplary root and crown for a single tooth or multiple roots and teeth. In addition, such typodont or generic models may be based on different configurations of teeth, for example, different sizes, shapes, and/or caps, different types of teeth, such as molars, bicuspids or canines, and/or different occlusal patterns or characteristics, for example, overbite, underbite, skewed or other like misalignment patterns.

As such, generic models for any type of teeth characteristic or type may be provided and used, allowing great flexibility in specializing for different teeth structures, occlusal patterns and characteristics of a patient. In addition, any conventional devices, systems and/or methods for the scanning of physical models, such as typodonts, to generate data may be used, such as known techniques for generating initial digital data sets (IDDS), including that set forth in U.S. Pat. No. 6,217,325, assigned to Align Technology, Inc., which is herein incorporated by reference, in its entirety, for all purposes.

To reduce the amount of data and/or filter out any undesirable data after such acquisition of data from the typodont or generic tooth model, the decimating of data (304) may be conducted, such as the removal or deletion of data or otherwise the finding of optimal data values through the elimination at a constant fraction of the scanning data; however, the decimating of data (304) may also be omitted or otherwise replaced by any filtering or data enhancement techniques.

Figure 3B:
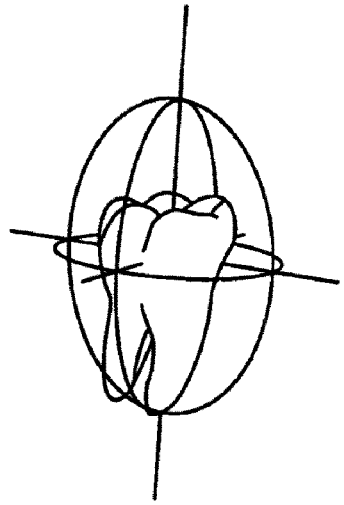
Figure 3C:
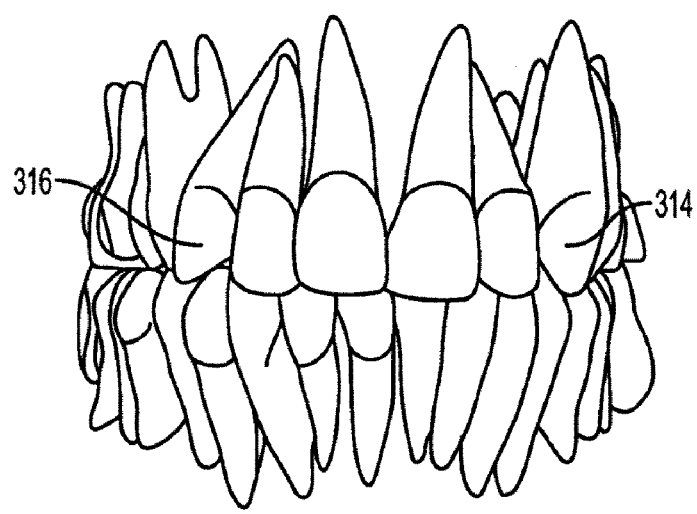

Whether or not the scanned data is decimated, the developing of a generic tooth coordinate system (306) may be undertaken, such as to setup or develop a generic tooth coordinate system as illustrated in FIG. 3B. The coordinate system may be set-up automatically and/or adjusted manually, using any conventional or later developed techniques for setting up coordinate systems of an object.

Upon generation of a coordinate system for a generic tooth, the constructing of a digital generic tooth model (308) including root and crown may be conducted for an individual tooth and/or two or more teeth. Such constructing of digital tooth models may include any methodology or process for converting scanned data into a digital representation. Such methodology or processes may include, for example, those disclosed in U.S. Pat. No. 5,975,893, entitled "Method and System for Incrementally Moving Teeth" assigned to Align Technology, Inc., herein incorporated by reference, in its entirety, for all purposes. For example, with reference to an overall method for producing the incremental position adjustment appliances for subsequent use by a patient to reposition the patient's teeth as set forth in U.S. Pat. No. 5,975,893, as a first step, a digital data set representing an initial tooth arrangement is obtained, referred to as the IDDS.

After construction of the generic tooth digital model (308), the identifying of the gingival curve (310) may be conducted to identify the gum lines and/or root association. Such identification may include any conventional computational orthodontics methodology or process for identification of gingival curves, now known or hereinafter derived. For example, the methodologies and processes for identification of gingival curves may include those disclosed in U.S. Pat. No. 7,040,896, entitled "Systems and Methods for Removing Gingiva From Computer Tooth Models", and assigned to Align Technology, Inc. (the "'896 patent") and U.S. Pat. No. 6,514,074, entitled "Digitally Modeling the Deformation of Gingival", and assigned to Align Technology, Inc. (the "'074 patent"), which are herein incorporated by reference, in their entirety, for all purposes, and the various patents disclosed in the '896 and '074 patents. In the '896 patent, for example, such a process for identification of gingival curves may include a computer-implemented method for separating a tooth from an adjacent structure, such as a gingiva, by defining a cutting surface, and applying the cutting surface between the tooth and the structure to separate the tooth in a single cut.

Having constructed the digital generic tooth model (308) and identified the gingival curve (310), one or more generic tooth template files may be created (312), such as the exemplary generic teeth template illustrated in FIG. 3C including substantially a complete set of teeth of a patient. Such generic teeth templates may then be used to allow for segmenting of crowns and landmark distribution on the generic teeth. In addition, such generic teeth templates may be used for one or more treatments, and/or replaced or updated with other generic teeth templates as desired. Moreover, such generic teeth templates may be created and/or stored for later use, and may be configured for various differences in patients, such as for children-based templates and adult-based templates, with the ability to have a plurality of templates that are specially created for the different types of teeth and related characteristics, sizes, shapes, and occlusal patterns or other features.

Referring again to FIG. 2, after generic teeth templates have been generated, automated segmenting of a generic crown from the generic root within the generic tooth template (210) may be conducted to prepare the generic tooth template for landmark creation. In this process, the crown portion of the generic tooth template may be parceled out and/or identified to allow mapping during landmark processes.

Figure 5A:
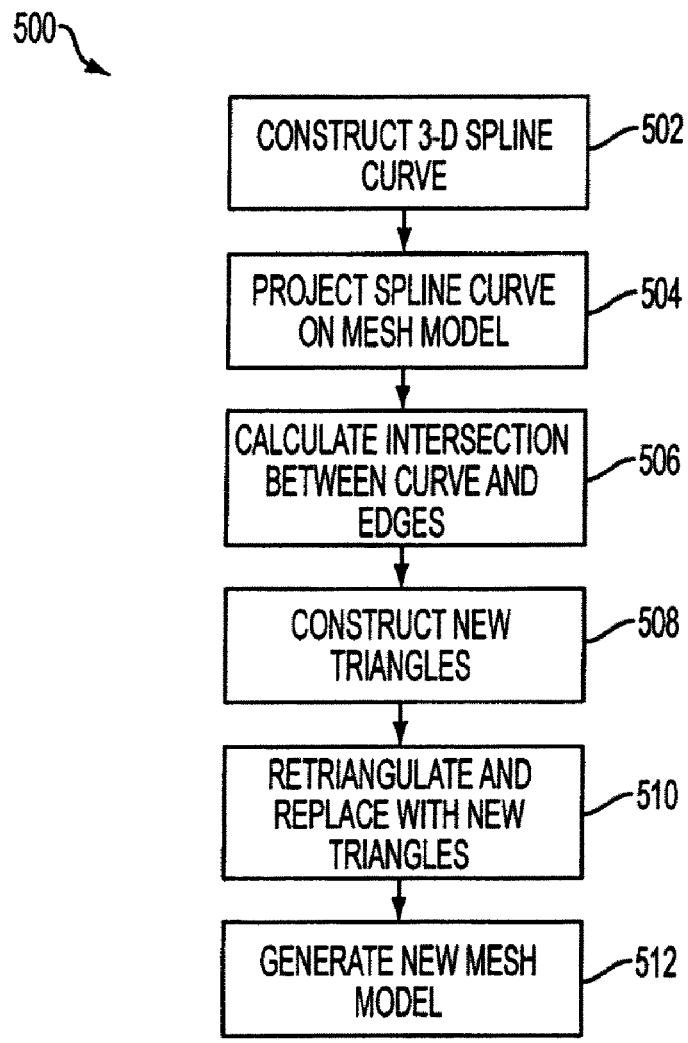
FIGS. 5A and 5B illustrate a flow diagram and a graphical representation for an exemplary method for root and crown mesh generation in accordance with an exemplary embodiment of the present invention.
Figure 5B:
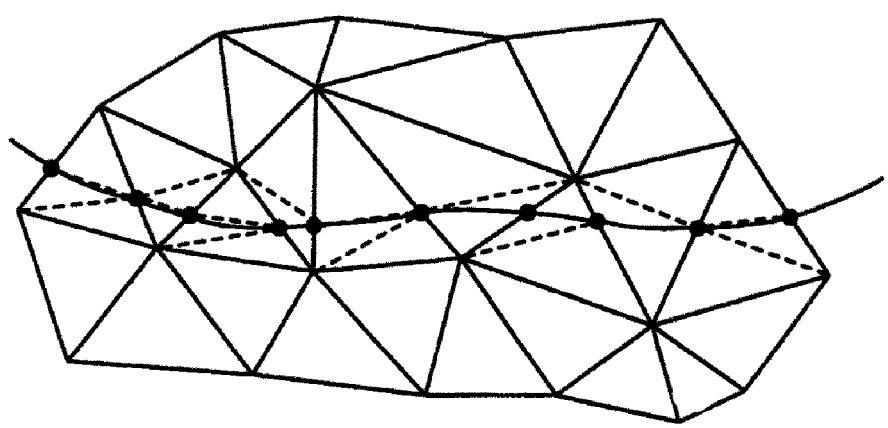

For the generic tooth, the crown geometry may be extracted from the generic tooth model. After such extraction or segmentation, a crown mesh may be generated. For example, with reference to FIGS. 5A and 5B, a process 500 for automated crown mesh generation may include the construction of a 3-D spline curve (502), where control points on the transition area between the tooth crown and root are used, such as that illustrated in FIG. 5B. Next, the projection of the 3-D spline curve on the tooth mesh model (504) may be conducted. A calculation of the intersection between the projected curve and the edges of triangle faces of the mesh (506) may then be made to facilitate the construction of new triangles (508). In this process, the three original vertices of the intersected triangle and the two intersection points may be used to construct three new triangles, such as by use of the Delaunay triangulation's max-min angle criterion. After such construction, the re-triangulation of the old intersected triangle and replacing that old triangle with the three newly generated triangles (510) may be conducted. Upon re-triangulation and replacement, the generation of a new crown mesh model (512) may be realized by removing all the faces below the projected curve, resulting in a segmented generic tooth crown. Processes 502, 504, 506, 508, 510 and 512 may be provided through any known conventional techniques for providing such functions, or hereinafter devised.

Figure 4A:
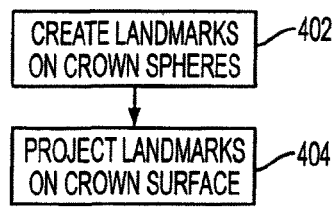
FIGS. 4A-4D illustrate a flow diagram and graphical representations of an exemplary method of automatic landmark generation for tooth crown in accordance with an embodiment of the present invention.
Figure 4B:
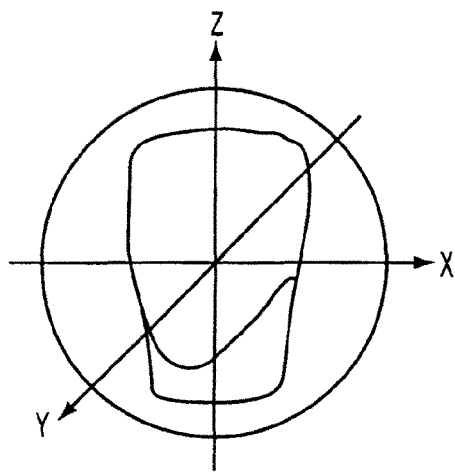

Referring again to FIG. 2, once the crown of the generic tooth template has been segmented, automated creation of landmarks on the generic crown (212) may be performed prior to morphing with the patient tooth crown model. In accordance with one embodiment, with reference to FIGS. 4A-4D, landmarks may be created on a crown sphere (402) and then the landmarks may be projected onto a crown surface (404). For example, a tooth crown may be mapped to a sphere by central projection, as illustrated in FIG. 4B. The landmarks may be created on the sphere through appropriate distribution on each of a plurality of cross-sections, for example, cross-sections through the Z-axis, perpendicular to the X-Y plane. As illustrated in a representative cross-section shown in FIG. 4C, a plurality of landmarks 406 may be created on a sphere 410 with appropriate distribution. The number of landmarks 406 may be determined through parameters such as the number of planes to be considered while sweeping through the Z-axis, and the number of points selected for each plane.

Figure 4C:
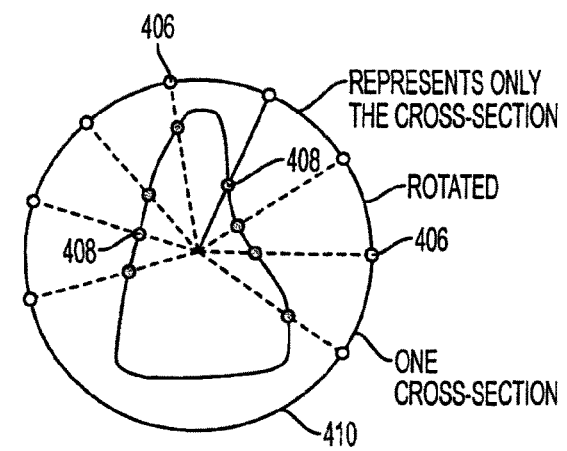
Figure 4D:
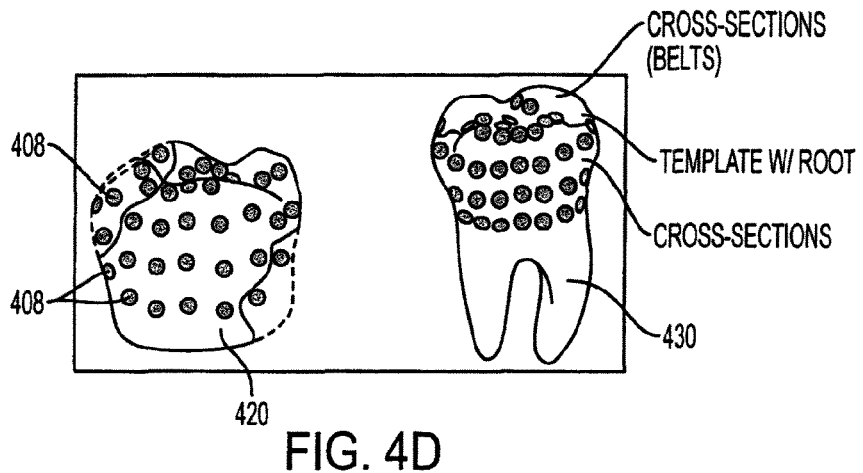

Once landmarks 406 are created on crown sphere 410 (402), landmarks 406 may be projected onto the crown surface, such as projected landmarks 408 projected onto the crown surface in FIG. 4C, and projected landmarks 408 illustrated in FIG. 4D that include projected landmarks 408 projected onto a scan of a patient's crown 420 and a generic tooth crown 430. Such an automated generation may be facilitated by one or more algorithms within a tooth modeling system, and may be computed for each patient tooth and generic tooth.

Note that a portion of the patient's crown surface image that has been partially blocked or has not yet erupted past the gingival line may be projected as a partial 3-D image. Thus, projected landmarks 408 are not directly projected to the patient's crown surface, but rather to a location that approximates the patient's crown surface as described below. The plurality of projected landmarks 408 on generic tooth crown 430 and the corresponding projected landmarks 408 on the patient tooth crown 420 may be used for calculating the morphing function as also described below.

Referring again to FIG. 2, method 204 for generating a patient tooth crown model may include the generation of an initial patient tooth model with at least a portion of the tooth structure missing (214), which includes generation of a crown tooth model having at least a portion of the tooth structure missing, automated detection of the remaining crown geometry (216) and the automated creation of landmarks on the patient crown tooth model (218). Generating the crown tooth model (214) may be realized by various known methods and techniques, including various conventional scanning techniques used in computational orthodontics for creating IDDS and the like.

For example, such an IDDS may be derived from the above methods and/or as set forth in U.S. Pat. No. 6,217,325, also assigned to Align Technology, Inc. In an exemplary embodiment, to obtain an IDDS, the patient's teeth may be scanned or imaged using well known technology, such as X-rays, 3D X-rays, computer-aided tomographic images or data sets, magnetic resonance images, and the like. Methods for digitizing such conventional images to produce data sets useful in the present invention are well known and described in the patent and medical literature.

Upon generation of the crown tooth model, automatic detection of the crown geometry (216) may be conducted to prepare the tooth model for creation of landmarks. For the patient tooth model, the crown geometry may be segmented from the entire tooth using any conventional process for segmentation of crowns from teeth. In one embodiment, the occlusal part of patient's crown geometry is available from the initial patient tooth model. An appropriate template may be selected from a library of crowns of the same tooth type based on the relative position of the occlusal features. The template selected may be scaled and positioned so that the missing portion of the patient's crown may be approximated as closely as possible. A threshold or envelope is established. Thus, points on the patient's tooth model that are a distance outside of the established threshold are considered as not belonging to the crown. Accordingly, projected landmarks may be placed only on the portions of the patient's crown that fall within the threshold. Only the corresponding landmarks are placed on the generic crown model of the same tooth. These landmarks are used for the subsequent morphing.

Thus, upon detecting the crown geometry, the automated creation of landmarks on the patient crown tooth model may be provided, such as the techniques (212) used on the generic crown model, for example, those illustrated in FIGS. 4A-4D.

Upon generation of the generic tooth model (202) and the crown tooth model (204), generation of the complete tooth model (206) may be conducted through combining or merging of the generic tooth model with the corresponding patient tooth crown model.

In one embodiment, a method for generating a complete tooth model (206) may include calculating the morphing function (220), applying the morphing function to the generic crown model to calculate a morphed generic crown model (222), stitching the morphed generic crown model to the patient crown model (224), smoothing the morphed crown-to-patient crown transition areas (226), thereby completing the missing tooth structure, and conducting interactive adjustment of the completed patient crown, if necessary (228). Such processes may be completely conducted for individual teeth before proceeding to any other teeth, conducted concurrently, or any other combination thereof. More specifically, an initial morphing function, which is used to determine a morphed central axis, may be calculated using crown landmarks from the patient crown tooth model and a generic crown model or a digitally mirrored contralateral tooth model. A central axis of the generic crown model or the digitally mirrored contralateral tooth model is determined and repositioned so as to be tangential to the morphed central axis. The repositioned central axis is then scaled to be substantially equal to the morphed central axis in a direction along a z-axis (see FIG. 4B). A final morphing function is then calculated through use of the crown landmarks from the generic crown model or the digitally mirrored contralateral tooth model and the patient crown model, and this final morphing function is applied to the generic crown model to calculate a morphed generic crown model.

In one embodiment, a thin-plate spline may be used to calculate the morphing function (220) by using the projected landmarks 408 (FIG. 4C). Use of such a thin-plate spline may minimize the deformation energy effects, for example, minimize the degree or extent of bent in the resulting surface between created landmarks 408. The deformation energy is defined as:

$$\int\int_{R^2}\left(\frac{\partial^2 f}{\partial^2 x^2}\right)^2 + 2\left(\frac{\partial^2 f}{\partial x \partial y}\right)^2 + \left(\frac{\partial^2 f}{\partial^2 y^2}\right)^2 dx dy$$

Once the morphing function is calculated (220), the patient crown model may be calculated (222), such as by applying the morphing function on the generic tooth crown model.

Figure 6:
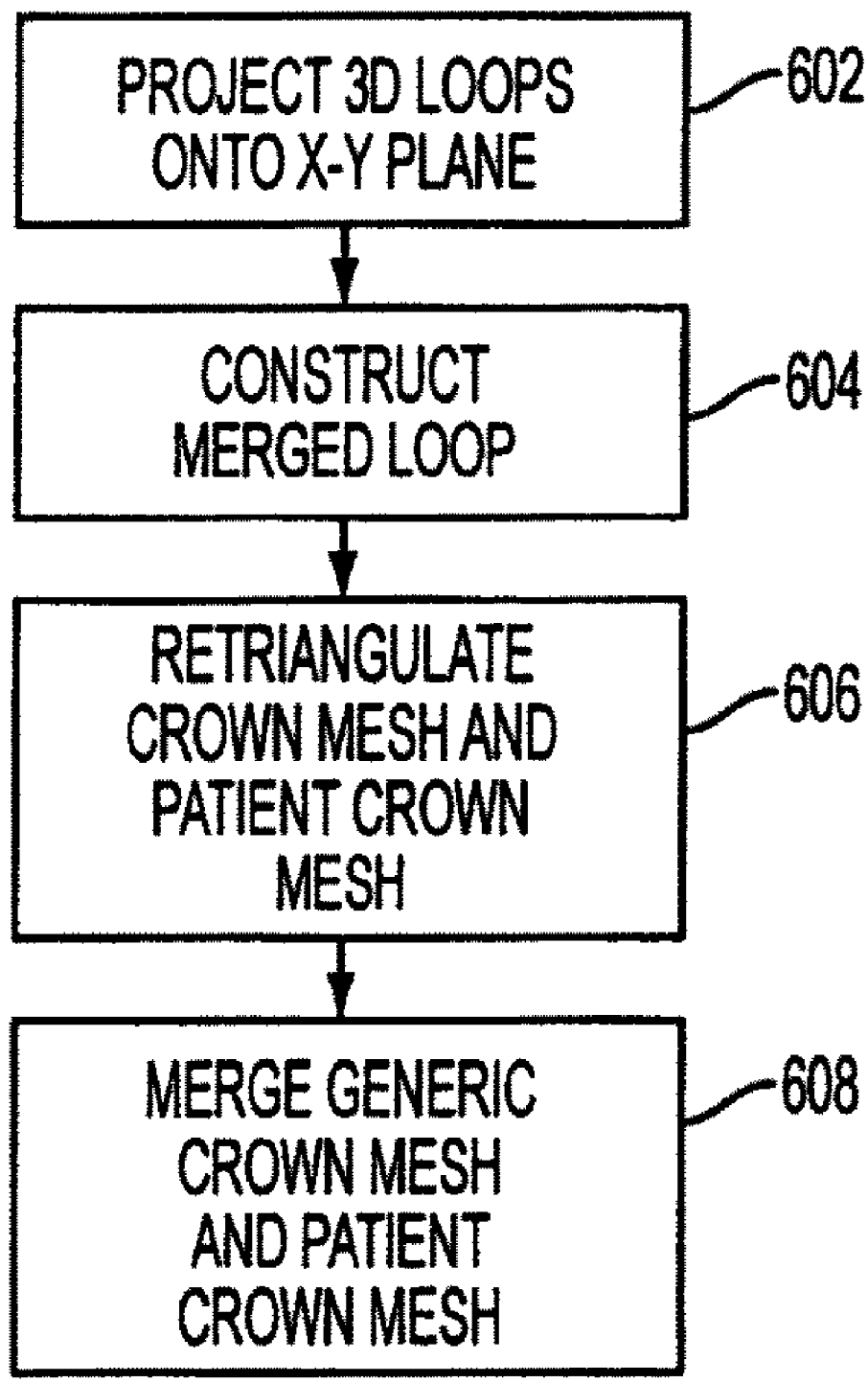
FIG. 6 illustrates a flow diagram for an exemplary method for meshing of the generic crown with the patient crown in accordance with an embodiment of the present invention.

After calculation of the patient tooth crown model (222) through morphing of the generic tooth crown model, the patient crown model may be stitched to the patient crown model to generate the complete 3-D tooth model (224). Generally, stitching occurs along the boundary of the missing crown surface of the patient's tooth model and the generic tooth crown model. To facilitate stitching, the generic crown mesh and the patient crown mesh are combined or merged. For example, with reference to FIG. 6, the stitching process includes the projecting of 3-D loops onto the X-Y plane (602). Since the projected loops are homogeneous to a circle, the loop vertices may be re-sorted by angle to construct a merged loop (604). Next, re-triangulation of the generic crown mesh and the patient crown mesh may be conducted (606). Upon re-triangulation, the generic crown mesh and the patient crown mesh may be merged (608) to obtain a topologically correct complete tooth crown mesh.

After stitching (224), the transition areas of the complete tooth model may be smoothed (226) to improve the model, for example, using a smoothing algorithm. The smoothing algorithm may operate as a filter to essentially remove "noise" from the stitched points within the transition area. In one embodiment, the smoothing algorithm may identify or target a first point, then observe neighboring points to tweak or otherwise adjust the first point to smooth out the stitching. The algorithm may be conducted for each tooth within the patient. Such an algorithm may also include various formats and structures for providing the smoothing function After generation of the complete crown model, the generated crown shape may vary from the actual crown shape due to the individual features of the patient. With reference again to FIG. 1A in accordance with an exemplary embodiment, further adjustment of the complete crown model for the tooth may be provided through detailed adjustment module 114. For example, additional patient tooth crown information regarding features or characteristics of the patient's actual crown, such as may be obtained from X-ray imaging information provided from radiograph 116, may be used by tooth modeling system 122 to address the variations in crown shape between the generic tooth crown and an the actual tooth crown shape for a patient so as to yield a tooth shape on complete tooth model 112 which more closely approximates the actual tooth shape of the actual teeth.

Such additional actual tooth crown information may include various formats and generated in various manners. For example, X-ray imaging information may include panoramic, periapical, bitewing, cephalometric or other like information, for facilitating further detailed modeling. In addition, since such X-ray imaging information generally comprises a 2D image, the X-ray information may be considered approximately as a 2D projection from the facial side to the lingual side. As a result, the further detailed adjustment is based on one-view information, where the algorithm makes the modeled tooth shape coincide with the actual tooth shape based on such one-view information.

Figure 7A:
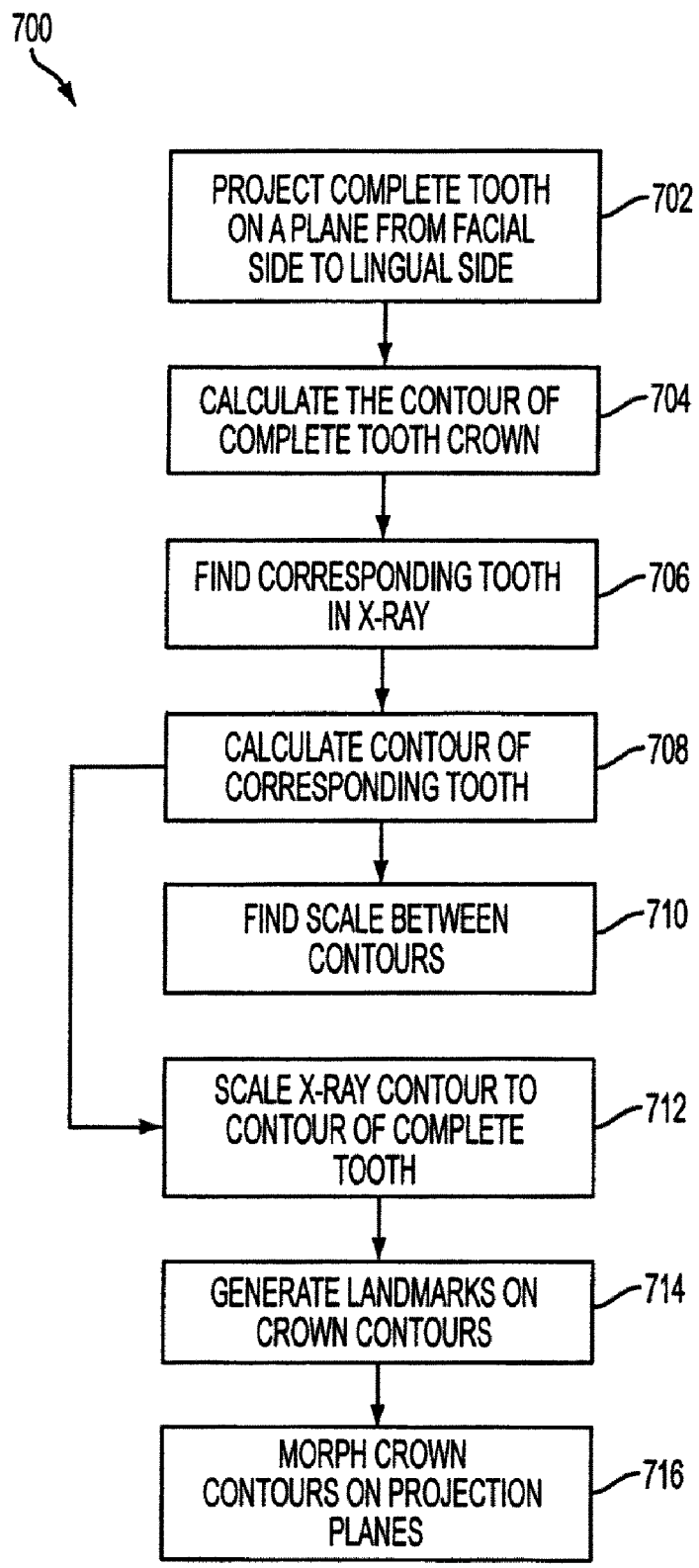
FIGS. 7A-7F illustrate an exemplary flow diagram and graphical representations for automatic complete tooth model adjustment using X-ray data in accordance with an exemplary embodiment of the present invention.
Figure 7B:
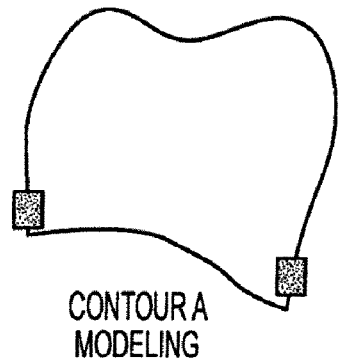
Figure 7C:
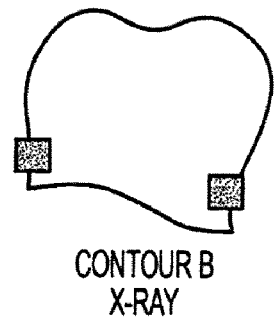

In one embodiment, as in FIG. 7A, a method 700 for detailed adjustment modeling may begin with the projection of the complete crown model, for example, one derived after combining/merging (206) of method 200, on a single plane, whose normal is from a tooth's facial side to a tooth's lingual side (702). Next, the contour of the complete crown may be calculated (704) and defined, such as the tooth crown contour A illustrated in FIG. 7B. The corresponding patient tooth crown may be identified from the X-ray information, such as from panoramic X-ray image (706), and the contour of the corresponding tooth crown may also be calculated from that X-ray image (708) and defined, such as the tooth crown contour B illustrated in FIG. 7C. Any conventional methodology or process for calculation and/or determination of contours may be readily used for determining the contours of tooth crown A and tooth crown B.

Next, the scaling in size between the complete tooth crown contour (contour A), and the corresponding patient tooth crown contour (contour B) may be determined (710), and then the corresponding patient tooth crown contour may be scaled to have the same crown contour as the complete tooth crown contour (712).

Figure 7D:
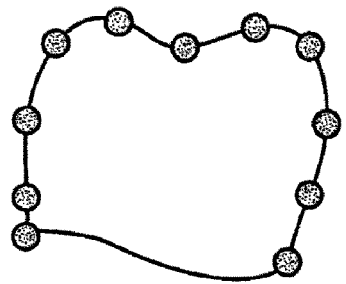
Figure 7E:
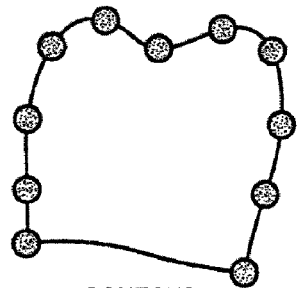
Figure 7F:
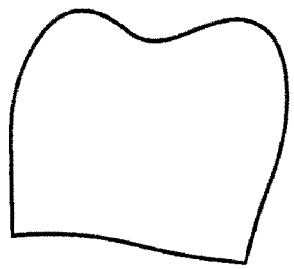

In accordance with an alternative embodiment, instead of scaling the patient tooth crown contour to the complete tooth crown contour (712), a thin-plate spline based morphing function may be used to deform the corresponding patient tooth crown contour to the complete tooth crown contour. For example, the morphing function may be calculated by the landmarks on the corresponding patient tooth crown contour and complete tooth crown contour. Landmarks may then be generated (714) on the complete tooth contour (contour A), and the corresponding patient tooth contour (contour B), such as illustrated with reference to FIGS. 7D and 7E. Based on the generated landmarks, and the calculation of the morphing function, the complete tooth contour may be morphed onto a projection plane (716), such as illustrated in FIG. 7F. Such morphing may be conducted through similar processes as disclosed in morphing/combining process 206, for example, by calculating a morphing function by landmarks (220) and applying the morphing function on the generic tooth crown (222). Accordingly, a complete tooth crown model for any one and/or all teeth of a patient, adjusted through an accounting of a patient's individual and/or specialized features and characteristics, may be realized.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, for example, various of the component and methodologies and/or steps may be deleted, modified, or combined with other components, methodologies and/or steps. Moreover, it is understood that various of the methods and steps disclosed herein, such as generating of IDDS, construction of 3D spline curves, identifying gingival curves or other processes may also include any other conventional techniques, or any later developed techniques, for facilitating such methods and steps. These and other functions, methods, changes or modifications are intended to be included within the scope of the present invention, as set forth in the following claims.

What is claimed is:

1. A computer-implemented method for modeling a complete tooth of a patient to facilitate dental and/or orthodontic treatment comprising:
   generating a first set of digital data representing a first digital tooth model of a first patient tooth including a first crown component, said first set of digital data representing only a partial portion of a surface of said first crown component;
   generating a second set of digital data representing a digitally mirrored contralateral tooth model of a second patient tooth that is a contralateral patient tooth to the first patient tooth, the contralateral tooth model including a second crown component, said second set of digital data representing a complete surface of said second crown component; and
   combining said first set of digital data and said second set of digital data to create a third set of digital data representing a complete digital tooth crown model of the first patient tooth.

2. The computer-implemented method according to claim 1, wherein generating the second set of digital data representing the digitally mirrored contralateral tooth model including the second crown component comprises:
   providing the digitally mirrored contralateral tooth model including a root component and the second crown component; and
   segmenting said second crown component from said root component within said digitally mirrored contralateral digital tooth model.

3. The computer-implemented method according to claim 1, wherein the combining comprises smoothing a transition area between the combined first set of digital data and the second set of digital data to create the complete digital tooth crown model of the first patient tooth.

4. The computer-implemented method according to claim 1, wherein the combining further comprises conducting interactive adjustment of the combined first set of digital data and the second set of digital data to create the complete digital tooth crown model of the first patient tooth.

5. The computer-implemented method according to claim 1, wherein the combining further comprises:
   using crown landmarks from said digitally mirrored contralateral tooth model and said first digital tooth model to calculate an initial morphing function used to determine a morphed central axis;
   repositioning a central axis of said digitally mirrored contralateral tooth model to be tangent to said morphed central axis;
   scaling said repositioned central axis of said digitally mirrored contralateral tooth model to be substantially equal to said morphed central axis in a z-direction; and
   calculating a final morphing function through use of the crown landmarks from said digitally mirrored contralateral tooth model and said first digital tooth model.

6. A computer-implemented method for modeling a complete tooth of a patient to facilitate dental and/or orthodontic treatment comprising:
   generating a first set of digital data representing a first digital tooth model of a first patient tooth including a first crown component, said first set of digital data representing only a partial portion of a surface of said first crown component;
   generating a second set of digital data representing a digitally mirrored contralateral tooth model of a second patient tooth that is a contralateral patient tooth to the first patient tooth, the contralateral tooth model including a root component and a second crown component, said second set of digital data representing a complete surface of said second crown component;
   combining said first set of digital data and said second set of digital data to create a third set of digital data representing a complete digital tooth crown model of the first patient tooth; and
   segmenting said second crown component from said root component within said digitally mirrored contralateral digital tooth model.

7. The computer-implemented method according to claim 6, wherein the combining comprises smoothing a transition area between the combined first set of digital data and the second set of digital data to create the complete digital tooth crown model of the first patient tooth.

8. The computer-implemented method according to claim 6, wherein the combining further comprises conducting interactive adjustment of the combined first set of digital data and the second set of digital data to create the complete digital tooth crown model of the first patient tooth.

9. The computer-implemented method according to claim 6, wherein the combining further comprises:
   using crown landmarks from said digitally mirrored contralateral tooth model and said first digital tooth model to calculate an initial morphing function used to determine a morphed central axis;
   repositioning a central axis of said digitally mirrored contralateral tooth model to be tangent to said morphed central axis;
   scaling said repositioned central axis of said digitally mirrored contralateral tooth model to be substantially equal to said morphed central axis in a z-direction; and
   calculating a final morphing function through use of the crown landmarks from said digitally mirrored contralateral tooth model and said first digital tooth model.

* * * * *